United States Patent [19]

Elam

[11] 4,090,518
[45] May 23, 1978

[54] ESOPHAGO-PHARYNGEAL AIRWAY

[76] Inventor: James O. Elam, 6723 S. Euclid Ave., Chicago, Ill. 60649

[21] Appl. No.: 713,904

[22] Filed: Aug. 12, 1976

Related U.S. Application Data

[63] Continuation-in-part of Ser. No. 607,267, Aug. 25, 1975, abandoned.

[51] Int. Cl.$^2$ .......................................... A61M 16/00
[52] U.S. Cl. ........................... 128/349 B; 128/350 R; 128/2.06 E; 128/351 R; 128/145.8
[58] Field of Search .......................... 128/145.5–145.8, 128/147, 351, 349 R, 349 B, 348 R, 349 BV, 350 R, 358 V, 2.06 E, 404, 419 D, 419 P, 418

[56] References Cited

U.S. PATENT DOCUMENTS

| 701,075 | 5/1902 | McCully | 128/349 R |
|---|---|---|---|
| 2,854,982 | 10/1958 | Pagano | 128/348 R |
| 2,857,911 | 10/1958 | Bennett | 128/147 |
| 3,046,988 | 7/1962 | Moreau et al. | 128/325 |
| 3,322,126 | 5/1967 | Rusch et al. | 128/351 |
| 3,326,207 | 6/1967 | Egan | 128/2.06 E |
| 3,407,817 | 10/1968 | Galleher, Jr. | 128/351 |
| 3,417,744 | 12/1968 | Mishkin et al. | 128/349 B |
| 3,460,541 | 8/1969 | Doherty | 128/351 |
| 3,543,751 | 11/1967 | Sheffer | 128/348 |
| 3,683,908 | 8/1972 | DonMichael et al. | 128/145.7 |
| 3,716,059 | 2/1973 | Welborn et al. | 128/419 D |
| 3,766,924 | 10/1973 | Pidgeon | 128/349 B |
| 3,837,347 | 9/1974 | Tower | 128/404 |
| 3,841,319 | 10/1974 | DonMichael et al. | 128/28 |
| 3,862,635 | 1/1975 | Haraujuneian | 128/351 |
| 3,874,377 | 4/1975 | Davidson | 128/145.5 |
| 3,881,479 | 5/1975 | Carden | 128/349 B |
| 3,889,688 | 6/1975 | Eamkoow | 128/351 |
| 3,905,361 | 9/1975 | Hewson et al. | 128/145.5 |

FOREIGN PATENT DOCUMENTS

| 1,505,607 | 12/1967 | France | 128/349 B |
|---|---|---|---|
| 2,426,425 | 10/1975 | Germany | 128/419 D |
| 708,477 | 5/1954 | United Kingdom | 128/349 B |
| 1,040,425 | 8/1966 | United Kingdom | |

OTHER PUBLICATIONS

I. Schandinischky et al., "Technical Note-The Shape Conforming Electrode"; Med. & Biol. Engng. vol. 7, pp. 341–343, Pergamon Press 1969, 12/28/68.

Guiffrida, Joseph G. et al., "Intubation of the Esophagus–Its Role in Preventing Aspiration Pneumatic and Asphyxial Death", American Journal of Surgery, vol. 93, Feb. 1957.

Farley, Marilyn, "The Esophageal Obturator Airway", Respiratory Therapy, Nov./Dec., 1973.

"Esophageal Obturator Airway", JAMA, p. 853, Feb. 18, 1974.

Primary Examiner—Kyle L. Howell
Assistant Examiner—Henry J. Recla
Attorney, Agent, or Firm—Hosier, Niro & Daleiden, Ltd.

[57] ABSTRACT

An esophago-pharyngeal airway having at least one inflatable cuff for sealing the nasal passage by urging the soft palate against the posterior nasopharyngeal wall and sometimes another inflatable cuff engageable with the wall of the esophagus to prevent ventilation of the stomach and possible aspiration of the stomach's contents depending upon the selected use. Either or both of the cuffs may be continuously inflated during use of the airway or may automatically inflate and deflate with each respiratory cycle to insure non-traumatic extubation when a tracheal tube is substituted for the esophago-pharyngeal airway. An air tube extends through one of the cuffs and a gastro-esophagus tube extends through both of the cuffs. In one form of the device, the lower cuff is adapted to be positioned in the esophagus between the heart and sternum and is provided with means not only for electronically monitoring heart operation but also for defibrillating the heart when the device is in place for performing artificial respiration.

39 Claims, 16 Drawing Figures

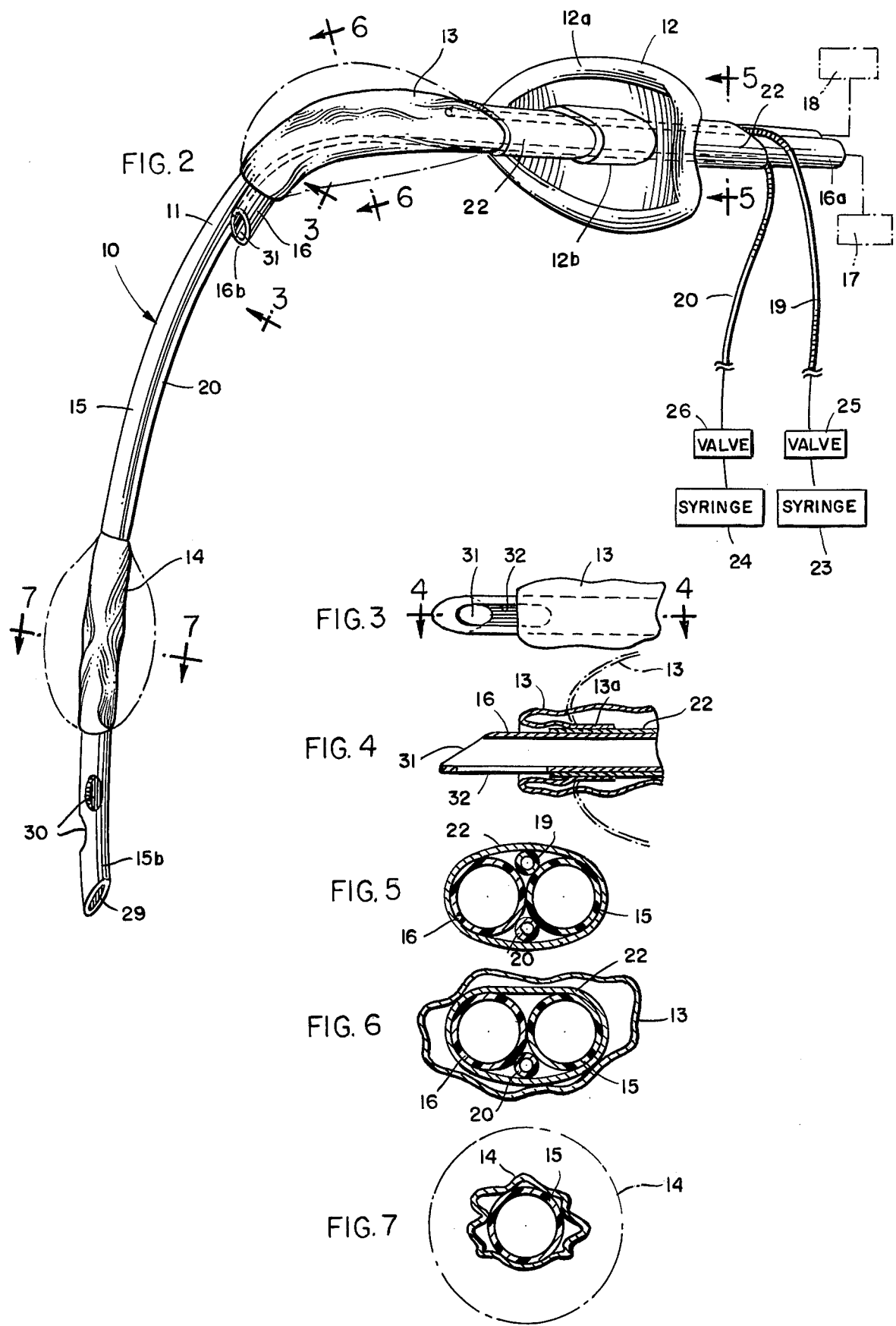

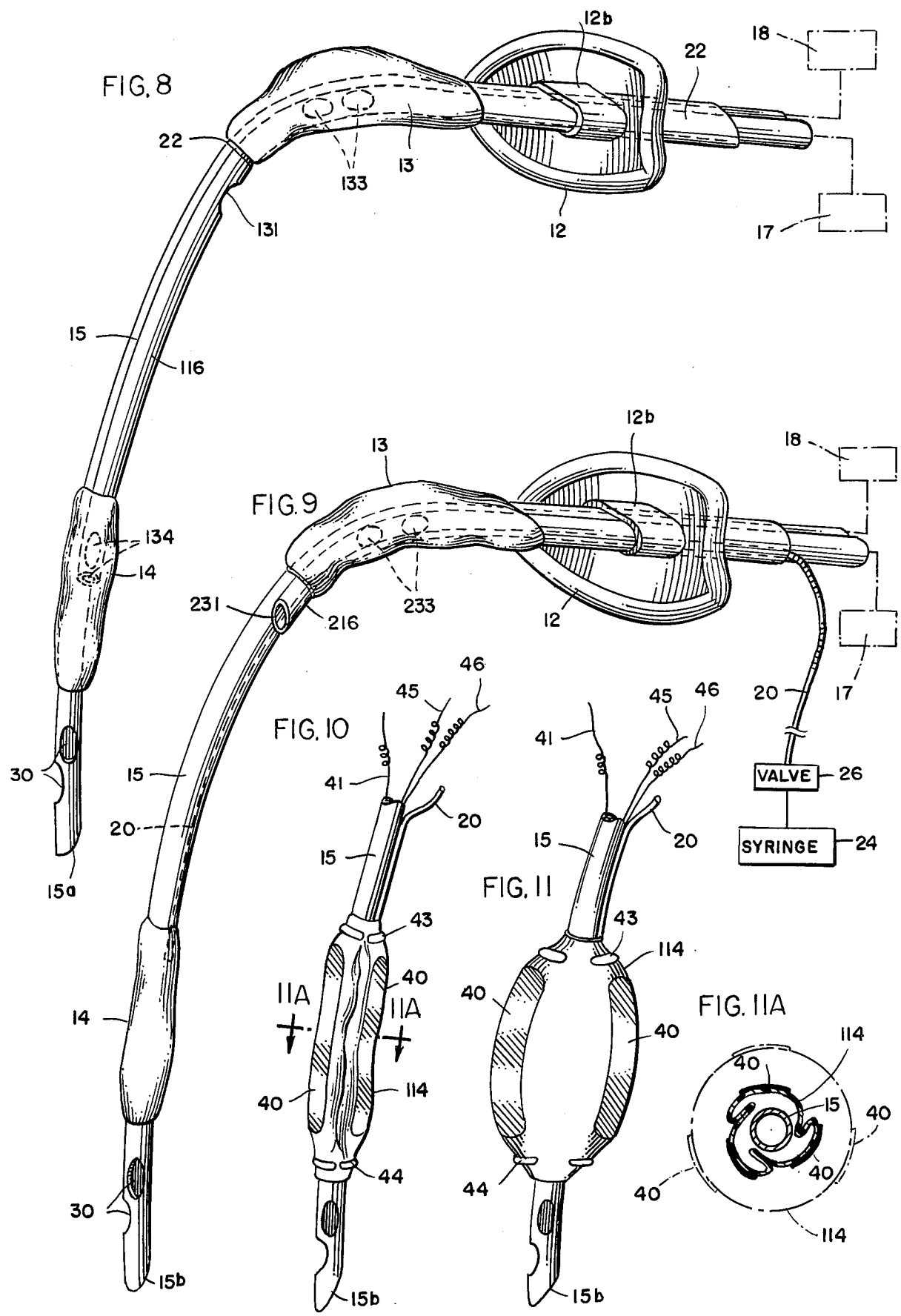

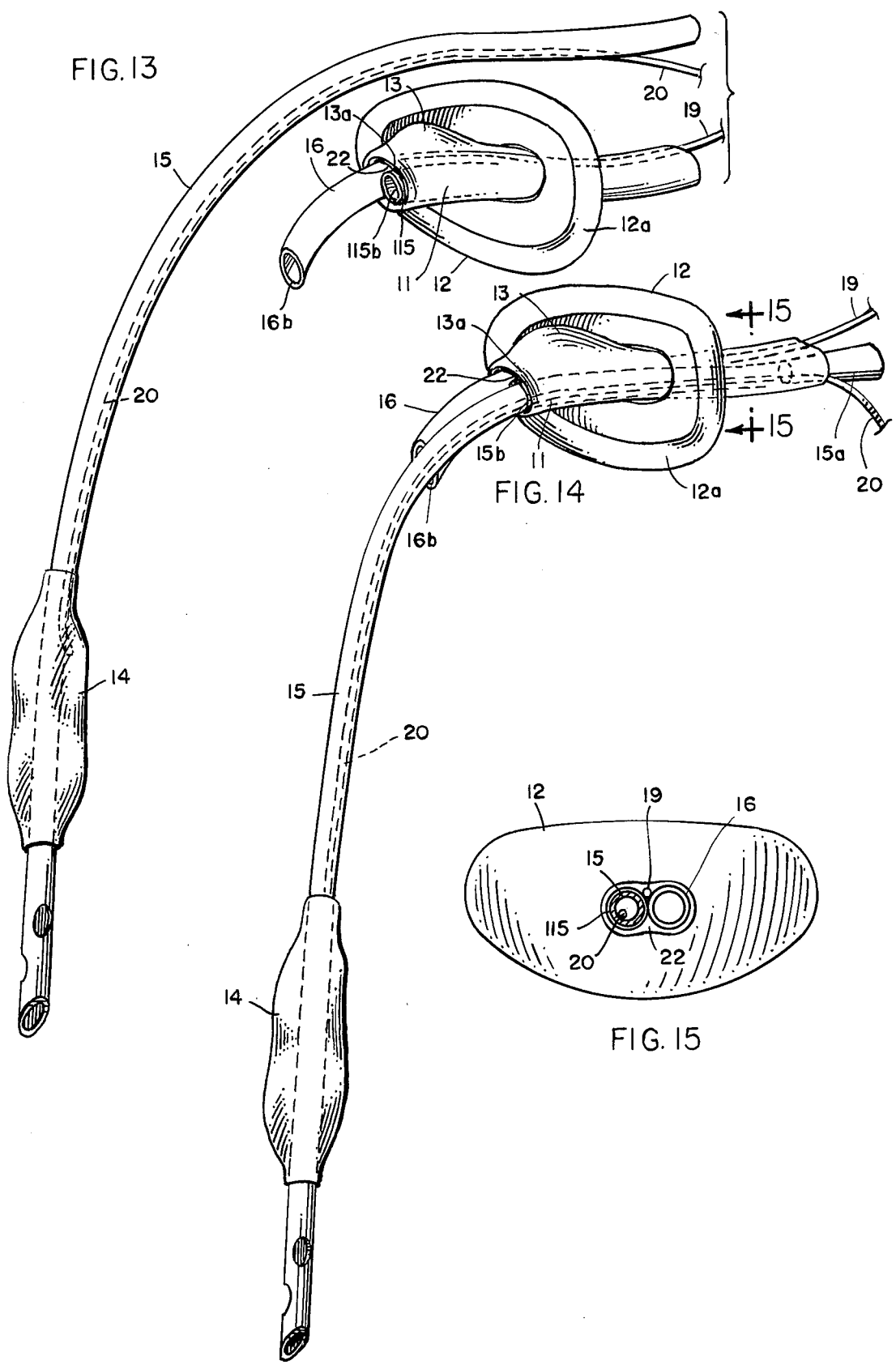

ESOPHAGO-PHARYNGEAL AIRWAY

RELATED APPLICATION

This is a continuation-in-part of copending U.S. Ser. No. 607,267 filed Aug. 25, 1975, now abandoned, titled "Esophago-Pharyngeal Airway".

BACKGROUND

Esophageal intubation and obturation to prevent aspiration of stomach contents during resuscitation has been disclosed by Giuffrida and Bizzarri, Amer. J. Surgery, Vol. 93, 329–334 (1957), Farley, Respiratory Therapy, pp. 95–99 (Nov./Dec. 1973), and in U.S. Pat. Nos. 3,683,908 and 3,841,319. A typical esophageal obturator airway consists of a cuffed endotracheal tube mounted through a face mask and provided with multiple openings in the upper one third of the tube at the level of the pharynx. In use, the tube is passed into the esophagus, the mask is seated upon the face, and the cuff is inflated. When mouth-to-tube or bag-valve-tube ventilation is performed, the air is discharged through the pharyngeal openings in the tube and passes down the trachea since the esophagus is blocked. The inflated cuff prevents gastric distension (by air) and regurgitation during resuscitation.

Esophageal obturator airway systems find increasing use in the emergency treatment of unconscious patients whose breathing has stopped or appears inadequate or likely to stop. Such resuscitation is needed for persons exposed to drowning or asphyxiation, who suffer from cardiac arrest, or who suffer from interrupted or inadequate respiration for any of a variety of other reasons.

In the treatment of cardiac arrest cases, external cardiac compression is commonly exerted in an effort to restore heart activity. Such compression promotes regurgitation and excessive lung inflation and promotes gastric inflation which also promotes regurgitation, with the potential danger that the stomach's contents might be aspirated into the lungs. The use of an esophageal obturator airway prevents occlusion of the natural airway, prevents aspiration, and assures the delivery of a high concentration of oxygen to the lungs. While the placement of such a system should be undertaken only be trained personnel, the procedure is one which does not require surgery (tracheotomy) or the services of an anesthetist with hospital facilities (unlike the insertion of a standard tracheostomy tube). Hence, the procedure is one which is being found increasingly useful in the emergency treatment of cardiac arrest patients.

Despite their advantage, prior esophageal obturator airway systems do have notable shortcomings and disadvantages. For one thing, proper ventilation of the patient depends on avoiding leakage of substantial quantities of oxygen through the mouth and nose. Quite obviously, is oxygen for resuscitation does not enter the patient's trachea but instead escapes through his nose or mouth, no artificially-induced respiration can occur. In an effort to reduce such backflow, a mask is ordinarily placed over the patient's nose and mouth; however, such masks are at best only partially effective. The problems are complicated by the fact that there are limitations on the maximum cross sectional dimensions of the main air tube, and the cuff-inflating tube and stomach tube with which it is associated, so that if adequate ventilation is to be provided, the loss of air needed for resuscitation must be avoided.

Other disadvantages of prior esophageal obturator airway systems include inadvertent tracheal intubation, blocking ventilation of the lung and laceration of the esophagus when the system is removed without deflating the esophageal balloon. The effectiveness of the inflated cuff as a sealing element requires that it firmly engage the esophageal wall; unfortunately, such firm engagement may have its own undesirable side effects since the inflated balloon is too large to pass throughout the upper esophagus without causing laceration.

Other references illustrating the state of the art are U.S. Pat. Nos. 3,889,688, 3,222,126, 3,460,541, 3,407,817, 3,826,635, 3,046,988 and 2,854,982.

SUMMARY

This invention is concerned with an improved esophago-pharyngeal airway system which overcomes the aforementioned defects and disadvantages of prior systems and which, in addition, may provide entirely new functions and results not found in any current system. Specifically, the esophago-pharyngeal airway system of this invention is relatively simple to insert and, when fully in place, effectively seals not only the esophagus but also the nasal and oral passages to that leakage of oxygen for resuscitation is kept to a minimum.

In general, an airway device embodying this invention includes a pair of inflatable cuffs or balloons, one of the cuffs being distally positioned for sealing engagement (upon inflation) with the esophageal wall and the other cuff being proximally positioned for engagement with the soft palate. The proximal cuff when properly positioned is disposed at the rear of the oral cavity and, upon inflation, urges the soft palate upwardly into sealing engagement with the posterior nasopharyngeal wall. Therefore, the proximal cuff performs the multiple functions of contributing to proper retention of the device and sealing against the leakage of oxygen (or other gases) through the patient's nose. A movable oral flange seals the mouth.

The device can include a relatively long esophageal tube (on which the esophageal obturator cuff is mounted) and a relatively short air tube which has its distal end positioned at the entrance to a patient's trachea when the device has been properly inserted. Preferably, the two tubes are used in juxtaposition; that is, they are in side-by-side non-concentric relation. When viewed in section, the double-barreled device has a greater lateral dimension (in its proximal region) than vertical dimension. Because of its superior anatomical conformance and other optional features, insertion of the device is facilitated and, when fully inserted for use, such device provides relatively large passages for air (oxygen) flow and for gastric drainage or the like.

One or both of the cuffs may be inflated (and deflated) through passages which are separate from the main passages of the juxtapositioned drainage and air tubes. It has been found, however, that either (or both) of the cuffs may be alternately inflated and partially deflated with each respiratory cycle. In such a construction, the repetitiously inflatable-deflatable cuff is supplied by air from the main air tube, the port or ports placing such cuff in communication with the air tube being dimensioned so that air supplied to the patient first enters and inflates the cuff, and when the flow is reversed, the air is first extracted from the cuff. The alternate contraction of the cuff allows blood circulation in the area engaged by the cuff and, in those constructions in which the proximal nasopharyngeal-sealing cuff is repetitiously inflatable and deflatable, permits the exhalation of air through the natural nasal pathway. In effect, the proximal cuff or balloon cooperates with the nasopharyngeal surfaces to perform a valving function and to the extent that a natural pathway is formed for exhalation it is possible to utilize any of a variety of air-supplying devices or techniques for inflating a patient's lungs. Stated differently, the resuscitation equipment may be only rudimentary and need not include the usual non-breathing valve to permit the expiration of air through the main air tube.

In a further embodiment of the invention, the esophageal obturator cuff remains continuously expanded (in contrast to being intermittently inflated and deflated) and is provided on its outer surface with a defibrillating electrode. Inflation of the cuff urges the electrode into firm engagement with that portion of the esophageal wall which is adjacent to the heart. Therefore, should defibrillation become necessary (a not-too-unlikely possibility since cardiac arrest constitutes a major use of esophageal obturator airways), electric countershock of the heart may be readily undertaken utilizing the esophageal electrode and an external electrode placed upon the patient's chest. It is particularly significant that such transesophageal defibrillation may be performed at far lower current levels than conventional external defibrillation procedures because the resistance of only one instead of two layers of skin is involved and because of the close proximity of the electrode to opposite sides of the heart, and that the electrical current path may be almost entirely limited to the cardiac muscles, unlike conventional defibrillation procedures which also affect skeletal (especially intercostal) muscles. The esophageal site for the electrode is subadjacent to the heart and does not involve the higher electrical resistance through the skin (for both electrodes in conventional defibrillation).

Other objects and advantages of the invention will be apparent from the specification and drawings.

DRAWINGS

FIG. 2 is a perspective view, shown partially schematically, of the device depicted in FIG. 1.

FIG. 3 is a fragmentary longitudinal view taken along line 3—3 of FIG. 2.

FIG. 4 is a sectional view taken along line 4—4 of FIG. 3 and revealing the attachment between the proximal balloon and the air tube which results in exposure of a lateral flow port when the balloon is expanded.

FIG. 5 is a sectional view taken along the line 5—5 of FIG. 2.

FIG. 6 is a sectional view taken along line 6—6 of FIG. 2.

FIG. 7 is a transverse cross section taken along line 7—7 of FIG. 2.

FIG. 8 is a perspective view illustrating a modified device embodying the invention.

FIG. 9 is a perspective view of a third embodiment of the invention.

FIG. 10 is a fragmentary perspective view illustrating the esophageal cuff construction of a fourth embodiment.

FIG. 11 is a perspective view similar to FIG. 10 but showing the esophageal cuff in expanded condition.

FIG. 11A is a slightly-enlarged sectional view along 11A—11A of FIG. 10.

FIG. 13 is a perspective view illustrating a partially unassembled fifth embodiment of the invention.

FIG. 14 is a perspective view of the fifth embodiment fully assembled.

FIG. 15 is a sectional view taken along line 15—15 of FIG. 14.

DESCRIPTION

Figure 1:
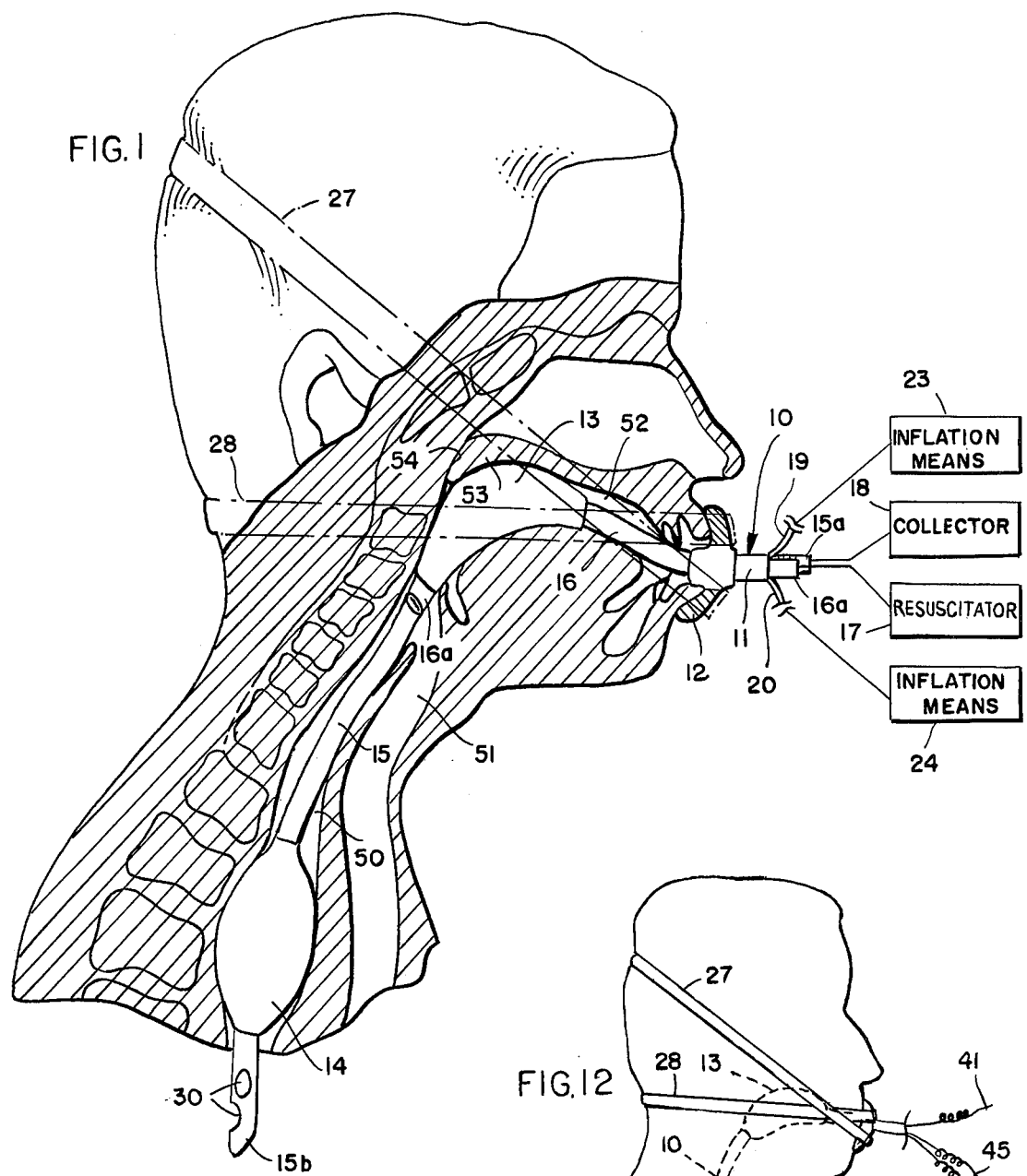
FIG. 1 is a diagrammatical sagittal sectional view illustrating an esophago-pharyngeal airway system for this invention in operative position.

Referring to the embodiment illustrated in FIGS. 1–7, the numeral 10 generally designates an esophago-pharyngeal airway system or device having a tube assembly 11, an oral flange 12, a proximal oral cuff or balloon 13, and a distal esophageal cuff or balloon 14. The tube assembly 11 comprises a pair of main tubes preferably arranged in side-by-side relation; specifically, an elongated stomach drain tube 15 and a shorter air tube 16. The purpose of the air tube is to ventilate a patient's lungs and, for that purpose, the proximal end 16a of the air tube may be connected to any conventional resuscitator 17. It is to be understood, of course, that if such a resuscitator is unavailable a rescue worker may blow his breath directly into the proximal end of the air tube to induce artificial respiration of the patient. Also, while tube 16 is generally referred to as an air tube (and sometimes as a breathing or inflation tube), the "air" supplied to the patient through that tube may have a somewhat different composition or proportion of gases than atmospheric air. For purposes of this disclosure, the term "air" will be used even though the composition may be relatively high in oxygen or in other gases, or may contain one or more gases intended to produce anesthesia or other desired effects.

The proximal end 15a of drain tube 15 may be joined by any suitable connecting means (not shown) to a collector 18, such as a vomit bag, or to any syringe or other device for introducing fluids to the stomach for the purpose of flushing or otherwise treating the stomach. As shown most clearly in FIGS. 2 and 5, the juxtapositioned main tubes 15 and 16 are accompanied by a pair of smaller pilot tubes 19 and 20 for the passage of air (or other fluid) to and from the inflatable cuffs 13 and 14, respectively. The pilot tubes may extend along the upper ahd lower channels formed between the converging external surfaces of the contiguous main tubes (FIG. 5) and all four tubes may be integrally extended or otherwise secured together by any other suitable means. In the illustration given, the tubes are wrapped in a smooth tubular sheath 22 which is oval in cross section, with its major axis extending horizontally, because of the side-by-side relationship of the main tubes 15 and 16. All of the tubes may be formed of a relatively soft flexible non-irritating plastic material such as polyvinyl chloride or other flexible plastic material.

The pilot tubes 19 and 20 are adapted to communicate with suitable inflating means 23 and 24 which, as indicated in FIG. 2, may constitute conventional syringes. Operation is simplified if manually-operated valves 25 and 26 are interposed in lines 19 and 20 adjacent the syringes. Thus, in operation, once the cuffs have been inflated to the desired extent, the valves may be closed and the syringes associated with the cuffs may be disconnected from the lines. Operation can also include connecting a conventional manometer to valve 26 to monitor internal compression force. Deflation of the cuffs is achieved simply by opening the valves. Where such valves are used, it is believed apparent that inflation of the cuffs may be achieved by using only a syringe or other inflating device.

The oral flange 12 includes a generally oval-shaped portion 12a adapted to fit over a patient's lips to close the mouth opening as depicted in FIG. 1. The flange also includes a collar portion 12b which frinctionally but slidably receives sheath or extension 22. By shifting the oral flange along the sheath or extension 22, the distance between that flange and the oral cuff, and the distance between the flange and the digital end of breathing tube 16, may be adjusted to produce a suitable fit for users of different sizes and shapes. Headbands formed of Velcro brand straps, tape, or any other suitable materials may be extended about the wearer's head, as indicated in FIG. 1 by numerals 27 and 28, to hold the oral flange (and the device as a whole) in proper position and prevent leakage at the lips.

In one preferred form of the invention, the drain tube 15 is of sufficient length to extend through the esophagus 50 and into the stomach to provide more effective drainage for the stomach. A shorter drain tube may be provided if desired; however, it is essential in any event that the drain tube extend well into the esophagus and that the lower cuff 14 be oriented so that it may (upon inflation) sealingly engage the esophageal wall at a point intermediate the length of the esophagus. Cuff 14 is also spaced upwardly from the free distal end 15b of the drain tube. It will be observed that the tube is not only provided with a terminal opening 29 but also with lateral openings 30 adjacent its distal end to facilitate fluid flow for drainage of the stomach and esophagus and for flushing or supplying fluids to the stomach.

The esohageal cuff 14 comprises an expandable resilient tubular wall formed of suitable plastic material. In the form illustrated in the drawings, the non-stretchable tubular wall is a separate sheath which is sealed at its opposite ends to the outer surface of the drain tube 15; however, it is conceivable that the tubular well might be formed integrally with the drain tube. In its normal deflated state, the wall of the cuff lies in close proximity to the outer surface of the drain tube. Upon inflation, the cuff or balloon increases substantially in transverse size, as indicated by the broken lines in FIGS. 2 and 7, for sealingly engaging the wall of the esophagus (FIG. 1). Air for inflation and deflation of the esophageal cuff is carried by esophageal pilot tube 20 which communicates with the interior of the cuff and also with inflating means 24.

As shown in FIG. 2, the breathing tube 16 is substantially shorter than the drain tube 15, the breathing tube's distal end 16b being located at a point intermediate the length of the drain tube and, specifically, at the entrance to the larynx 51 when the device is properly positioned in a patient (FIG. 1). As already indicated, proper diimensioning of tube 16 for a given patient, so that the distal end 16b is positioned at the entrance to the trachea, is achieved simply by shifting the oral flange 12 into a selected position of adjustment along sheath or extension 22.

Sheath or extension 22 extends about the parallel main tubes to a point near the distal end 16b of the breathing tube. It will be noted from FIG. 4 that the distal end of the breathing tube is provided with terminal opening 31 and, in addition, at least one longitudinally-elongated opening 32 in the side wall of the tube.

The longitudinal elongation of opening 32 helps insure that proper ventilation of the patient will be achieved even if slight misadjustment of the device should occur, that is, even if a portion of the opening 32, or a portion (or all) of opening 31, should be blocked by engagement with the wall of the pharynx or esophagus. The oral cuff or balloon 13 is similar to the esophageal balloon and is sealed to the tube assembly just above (i.e., proximal to) the breathing tube's distal end. As illustrated in FIGS. 3 and 4, the distal end of the tubular resilient wall which forms the oral cuff or balloon may be reversely turned, and the inturned end portion 13a then secured to sheath or extension 22. Such a construction has the advantage of permitting the oral cuff to be positioned as close as possible to the distal end of the breathing tube without at the same time occluding the openings of that tube when the cuff is inflated (FIG. 4).

Pilot tube 19 communicates with the interior of the oral cuff or balloon to inflate and deflate that member. When the device is properly positioned the oral cuff is disposed in the rear of the oral cavity 52 and, the cuff bears upwardly continuously against the soft palate 53 to urge the soft palate into sealing engagement with the posterior nasopharyngeal wall 54. The oral balloon therefore performs the multiple functions of sealing the nasal passage, and assisting exhalation. The breathing tube 16 communicates directly with the patient's respiratory passages and, because of the inflated esophageal balloon, there is no danger that the contents of the stomach (or esophagus) might be aspirated. The result is a highly effective device for the emergency treatment of patients suffering from respiratory and/or cardiac arrest.

The embodiment of FIG. 8 is similar to the one already described except that the pilot tubes for inflating and deflating the esophageal and oral cuffs are omitted. Instead, breathing tube 116 continues downwardly, communicating at its distal end with the interior of esophageal cuff 14. Side openings or ports 133 extend through the wall of the breathing tube (and also through the wall of sheath 22 if the sheath continues through the oral cuff as shown) for inflation and deflation of the oral cuff. Similarly, openings or ports 134 at the distal end of the breathing tube communicate directly with the interior of esophageal cuff 14. An anterior opening 131 in the wall of the breathing tube immediately below the distal end of oral cuff 13 provides for patient ventilation.

If desired, a plurality of such ventilation openings 131 may be provided. It is important, however, that the resistance to the flow of air through opening(s) 131 be greater than the resistance to the passage of air through openings 133 and 134. In general, the combined area of openings 133 should exceed the area of opening(s) 131, and the combined area of openings 134 should likewise exceed the area of opening(s) 131. It is believed, however, that satisfactory results may be achieved even where such a size differential does not exist, depending in part on the location of the openings within the cuffs, the distances between those openings and ventilation opening(s) 131, and the resistance of the material of the cuffs to stretching or expanding when inflation is required. The critical factor is that the ports or openings be dimensioned to provide less resistance to the flow of cuff inflating air (through openings 133 and 134) than to the flow of ventilating air to the patient through opening(s) 131. As a result, when the device of FIG. 8 is inserted in the same manner as depicted in FIG. 1, cuffs 13 and 14 will alternately inflate and deflate as ventilating air flows to and from the patient. Furthermore, because of the differences in resistance to flow, cuffs 13 and 14 will inflate, bearing against the soft palate and esophageal wall, in advance of the flow of air under full inflation pressure to the patient's lungs. The esophageal cuff therefore prevents inflation of the stomach, and the oral cuff seals the nasal passage against the escape of lung-inflating air. The oral flange seals the lips.

the esophageal and oral cuffs of the embodiment illustrated in FIG. 8 not only inflate prior to the introduction of air under full inflation pressure to the patient's lungs, but such cuffs begin to deflate immediately as the flow of air through breathing tube 116 is reversed. The oral cuff therefore deflates prior to the full discharge of expiratory air from the patient's lungs. Such expiratory air is free to pass about the exterior of the partially or fully deflated oral cuff 13 and through the patient's nasal passages and nostrils. A natural supplemental airway for the discharge of respiratory air is therefore provided and, since pressure against the soft palate and the nasopharyngeal mucosa is relieved momentarily during each respiratory cycle, problems of necrosis and ischemia which might otherwise exist if an expansive force were maintained constantly against the esophageal, oral and nasopharyngeal walls are avoided.

The embodiment of FIG. 9 combines certain of the features of the two previously-disclosed embodiments. Specifically, the FIG. 9 form has a drain tube 15, esophageal cuff 14, pilot tube 20, and esophageal-cuff inflating means 24 and 26 identical to the embodiment described in connection with FIGS. 2–7; however, breathing tube 216 differs from the tube 16 to the extent that it is provided with lateral ports or openings 233 communicating directly with the interior of oral cuff 13 in the same manner as described in connection with the FIG. 8 embodiment. Thus, the oral cuff of FIG. 9 is inflated by respiratory air rather than by air from a separate balloon-inflating surface, and the oral balloon automatically inflates and deflates with each respiratory cycle in precisely the same manner as described in connection with the FIG. 8 construction. As already described with regard to the FIG. 8 embodiment, ventilation port(s) 231 is dimensioned relative to cuff-inflating ports 233 so that full inflation of the oral cuff precedes the flow of air under full ventilating pressure to the patient's lungs and, conversely, the oral cuff or balloon deflates to provide a supplemental natural airway for expiratory air. On the other hand, since the esophageal cuff 14 is inflated by air from a separate source, the cuff remains continuously inflated in the same manner described in connection with the embodiment of FIGS. 2–7.

It is believed apparent that the teachings in connection with the embodiments of FIGS. 2–7 and FIG. 8 might also be combined in an alternative fashion so that, instead of the esophageal cuff remaining continuously inflated during operation and the oral cuff being automatically inflated and deflated with each respiratory cycle, as described in connection with the FIG. 9 construction, just the reverse occurs, that is, the oral cuff remains continuously inflated during operation and the esophageal cuff is automatically inflated and deflated with each respiratory cycle.

Figure 12:
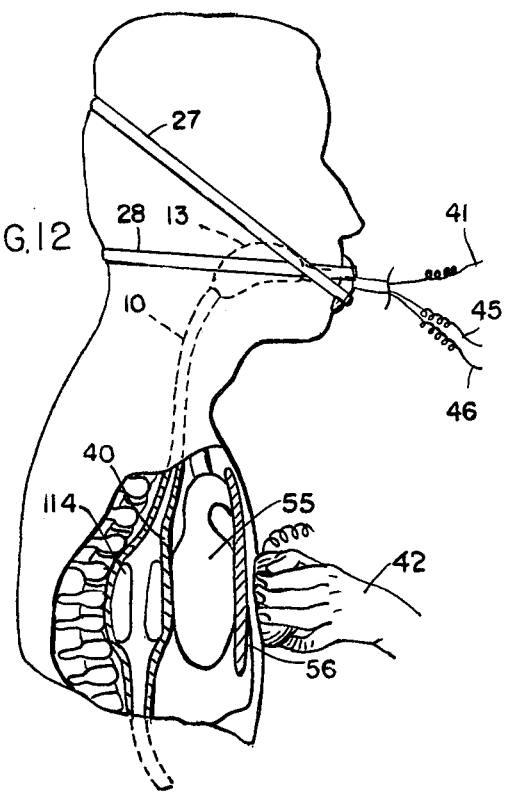
FIG. 12 is a schematic fragmentary sagittal section illustrating the esophageal cuff of FIGS. 10, 11 and 11A in operative position.

FIGS. 10–12 are directed to a modification of the esophageal cuff construction. As shown therein, the esophageal cuff 114 is equipped along its outer surface with one or more electrode elements 40. In the illustration given, the electrodes take the form of three several conductive strips 40 disposed in circumferentially-spaced relation (when the cuff is inflated) and extending longitudinally along substantially the entire length of the cuff. The strips are formed of flexible highly-conductive metal such as silver or copper and, since such strips are not stretchable in response to cuff-inflating forces, collapse of the cuff involves an overlapping or interleaving of the conductive and non-conductive wall portions as shown most clearly in FIGS. 10 and 11A. It is to be understood, however, that impregnation of the resilient and stretchable synthetic rubber or plastic material of the cuff with metallic particles or fibers is believed possible, thereby providing a wall construction that is both stretchable and conductive. In such a case, the entire intermediate portion of the cuff may constitute a homogeneous electrode.

Whether the defibrillating electrode takes the form of multiple strips (as shown) or only a single strip or surface, that electrode is connectable through lead 41 (which passes through the wall of the tube 15) to any suitable electrical source capable of providing an electrical pulse of sufficient intensity to produce defibrillation. It is to be understood that the electrode means 40 of the esophageal cuff is only one of two electrodes required for defibrillation; the other electrode 42 being located externally and being urged against the patient's chest to compress the heart 55 between the sternum 56 and the esophageal wall 57 (FIG. 12). Because the surfaces of both the internal and external electrodes are large, the current density required for defibrillation may be relatively low, thereby causing less cardiac muscle damage than in conventional electrical defibrillation procedures. Of particular importance is the fact that since the internal and external electrodes are spaced relatively closely on opposite (anterior-posterior) sides of the heart, the current requirements for defibrillation are far lower than if two conventional external electrodes are used. Thus, defibrillation may be achieved with current levels of apporoximately 15 to 20 watt seconds, whereas a conventional external difibrillation procedure involving only external electrodes may require 400 watt seconds or more. Furthermore, since the defibrillation current does not pass through skeletal muscle to any appreciable extent (the intercostal muscles do not lie directly between electrodes 40 and 42), the muscle effects, including the liberation of CPK and LDS enzymes associated therewith, are limited almost entirely, to those involving cardiac muscle rather than skeletal muscle.

Precise location of the internal electrode(s) 40 in relation to the external electrode 42 may be achieved by equipping the esophageal cuff 114 with EKG electrodes 43–44 adjacent opposite ends thereof. Such orienting and monitoring electrodes 43–44 may take the form of small patches or circumferential strips which are positioned on the outer surface of the cuff and which are insulated from each other and from electrode strips 40. Leads 45 and 46 extend through the wall of tube 15 to connect the strips or patches 43 and 44 with a conventional electrocardiograph. By observing the tracing (electrocardiogram) made by operation of the electrocardiograph as the cuff-equipped esophageal tube is inserted, an experienced operator may readily determine when the esophageal cuff has been advnaced to the point where it is in direct alignment with (i.e., directly behind) the heart. Also, since the EKG electrodes 43 and 44 remain in contact with the esophageal mucosa even when the cuff is inflated (FIG. 1), and since only the thin wall of the esophagus separates such electrodes from the heart, cardiac monitoring through the use of such electrodes may be carried out before, during and following trans-esophageal defibrillation.

It is believed apparent that where defibrillating and/or monitoring functions are to be performed, the esophageal cuff 114 should be continuously inflated with air or conducting fluid such as saline after it has been moved into operative position. The cuff would therefore be inflated by means of a pilot tube 20 in the same manner as disclosed with regard to the embodiments of FIGS. 2–7, or the embodiment of FIG. 9. For reasons already described, the provision of an oral cuff 13 is considered important; however, where the primary purpose of the device is that of defibrillating or monitoring, the oral cuff may be omitted.

The embodiment of FIGS. 13–15 is similar to the ones already described except that the tube assembly 11 is altered to facilitate insertion and provide for adjustment of the tube 15. Specifically, the device illustrated in FIGS. 13–15 has a drain tube 15, esophageal cuff 14, pilot tube 20, air tube 16, oral cuff 13, and pilot tube 19, essentially identical to the embodiment described in conjunction with FIGS. 2 through 7. The oral flange 12 is likewise essentially identical including a generally oval shaped portion 12a adapted to fit over a patient's lips but the flange (as shown in FIGS. 13 and 14) can optionally omit the collar portion but still frictionally and slidably receive the sheath or extension 22. By shifting the oral flange 12 along the sheath or extension 22 the distance between the flange and the oral cuff 13, and the distance between that flange and the distal end 16b of the air tube 16, may be adjusted to produce a suitable fit for users of different sizes and shapes.

Referring to FIG. 13, the tube assembly 11 still comprises a pair of tubes preferably arranged in side-by-side relation; however, the tubes are an air tube 16 and a shorter guide tube 115. The purpose of the guide tube 115 is to slidably receive the separate drain tube 15 for insertion into the esophagus and, for that purpose, the outer diameter of the drain tube 15 is slightly less than the inner diameter of the guide tube 115. It is to be understood, of course, that the guide tube 115 is also adapted to receive any elongated flexible tube which is adapted for insertion into the esophagus of a patient. The guide tube 115 is therefore well suited to slidably receive any other tubular instruments such as esophageal stethoscopes or defibrillating electrodes indicating the multiple uses available with the embodiment of FIGS. 13 through 15.

The guide tube 115 and the air tube 16 which can either be integrally extended or wrapped in the smooth tubular sheath 22, form an oval cross-section, with its major axis extending horizontally, because of the side-by-side relation of the tubes. The guide tube 115 is shorter than the air tube 16, the air tube's distal end 16b being located at the entrance to the larynx when the device is properly positioned in a patient. As already indicated, proper dimensioning of the air tube 16 for a given patient so that the distal end 16b is positioned at the entrance to the trachea is achieved simply by shifting the oral flange 12 into a selected position of adjustment along the sheath or extension 22.

The guide tube 115 and the air tube 16 are preferably parallel to a point near the distal end 115 of the guide tube. The oral cuff 13 is sealed to the tube assembly 11 just above (i.e., proximal to) the guide tube's distal end 115b. As illustrated in FIGS. 13 and 14, the distal end 13a of the tubular resilient wall which forms the oral cuff 13 may be reversely turned with the inturned end portion 13a then secured to the sheath or extension 22. The end 16b of the air tube 16 can then be spaced distally a substantial distance from the end 13a of the oral cuff 13. Such a construction has the advantage of permitting the oral cuff 13 to be properly positioned without at the same time occluding the opening of that tube when the cuff is inflated.

Referring to FIG. 15, the modified tube assembly 11 of FIGS. 13 and 14 can be better understood. The tube assembly 11 includes the guide tube 115 and the air tube 16 in side-by-side parallel relation encased in the sheath 22. The guide tube 115 is shown with an elongated flexible tube 15 inserted therein such as the drain tube illustrated in FIGS. 13 and 14. The tube 15 includes a tapered plug 15a at its proximal end which is preferably centrally apertured to permit outside communication with the tube 15. The tapered plug 15a has a maximum outer diameter greater than the inner diameter of the guide tube 115 to seal the opening of the guide tube 115 at its proximal end when the tube 15 is fully inserted. The pilot tube 19 extends along the upper channel formed between the converging external surfaces of the contiguous guide tube 115 and air tube 16 encased in the sheath 22. The pilot tube 20 is integral with the elongated flexible tube 15 and for the most part extends along the inner surface of that tube. Finally, the oral flange 12 frictionally but slidably receives the sheath 22 having a surface with a contour closely conforming to the contour of the sheath 22 for this purpose.

The advantages of the embodiment of FIGS. 13 through 15 can best be understood with reference to a description of its use. The tube assembly 11 is inserted into the patient's mouth until the distal end 16b of the air tube 16 is positioned at the entrance to the trachea. The oral flange 12 is then shifted into a suitable position against the lips to prevent any substantial leakage. The guide tube 115 can next slidably receive the elongated flexible tube 15 (as shown in FIG. 14) for insertion into the esophagus. After the tube 15 has been inserted and slidably adjusted into a desired position, the pilot tube 19 can be used to inflate the oral cuff 13 and the pilot tube 20 can likewise be used to inflate the esophageal cuff 14 in the event that a drainage tube or the like is being used with the tube assembly 11. When the device is in position with the cuff or cuffs inflated, oxygen can be administered to the patient through the air tube 16 while at the same time draining or treating the stomach, defibrillating the heart, or utilizing an esophageal stethoscope with a suitable elongated flexible tube 15 through the guide tube 115 depending upon the selected use for the device.

Other details of construction and operation of the embodiment of FIGS. 13 through 15 can be incorporated from the embodiments described hereinabove and illustrated in the other drawings. The tube assembly of this embodiment has advantages in providing for multiple usage of the device while at the same time facilitating insertion and adjustability of an elongated flexible tube in the esophagus. The various embodiments of the invention therefore provide many advantages depending upon structural details of the particular device.

While in the foregoing several embodiments of the invention have been disclosed in considerable detail, it is believed by those skilled in the art that many of these details may be varied without departing from the spirit and scope of the invention.

I claim:

1. An esophago-pharyngeal airway device adapted for insertion through the mouth and into the esophagus of an unconscious patient to provide separate passages for stomach drainage and artificial respiration, comprising an elongated flexible tube assembly including first tube means having a proximal end portion and a distal end portion for extending through said mouth and terminating in the stomach of a patient, and second tube means separate from said first tube means and having a proximal end portion adjacent the proximal end portion of said first tube means and a distal end portion for extending through the mouth and terminating proximal to the distal end portion of said first tube means and having an air flow port proximate the entrance of a trachea of a patient, said first tube means being a stomach drain tube and said second tube means being an air tube; said first and second tube means being disposed in close parallel relation; an inflatable and deflatable tubular oral balloon meeans extending about and sealed to said first and second tube means intermediate the end portions of said second tube means for engaging and urging the soft palate into sealing engagement with the posterior nasopharyngeal wall of a patient following insertion of said device and inflation of said oral balloon means; means for inflating and deflating said oral balloon means; an inflatable and deflatable tubular esophageal balloon means spaced distally from said distal end of said air tube and extending about and sealed to said drain tube for sealingly engaging upon inflation thereof, the wall of a patient's esophagus below the entrance to the trachea and above the stomach to prevent aspiration or refluxed stomach contents; said second tube means extending distally of said esophageal balloon means and terminating in at least one drainage-receiving opening at its distal end; and means for inflating and deflating said esophageal balloon.

2. The device of claim 1 in which an oral flange member is externally mounted upon said tube assembly adjacent the proximal ends of said tube means for sealingly engaging the face of a patient about the lips thereof.

3. The device of claim 2 in which said flange member is frictionally and slidably mounted upon said tube assembly.

4. The device of claim 1 in which said separate parallel tube means are disposed in side-by-side relation.

5. The device of claim 4 including securing means for maintaining the side-by-side relation of said separate parallel tube means.

6. The device of claim 4 in which said oral balloon means is sealingly secured at its ends to said tube assembly.

7. The device of claim 1 in which said air flow port is located distal to said oral balloon means.

8. The device of claim 7 in which said air flow port is disposed at the distal end of said air tube.

9. The device of claim 7 in which said port air flow is disposed intermediate the ends of said air tube.

10. The device of claim 9 in which said air tube is provided with an opening at its distal end which communicates with the interior of said esophageal balloon means: said opening being dimensioned larger than said air flow port so that the resistance to flow of air from the proximal end of said air tube and out through said opening is less than the resistance to the flow of air from said air tube proximal end and out through said port.

11. The device of claim 10 in which said air tube is provided with a second opening proximal to said air flow port and communicating with the interior of said oral balloon means; said openings being dimensioned larger than said port so that the resistance to the flow of air from the proximal end of said air tube and out through said openings is less than the resistance to the flow of air from said air tube proximal end and out through said port.

12. The device of claim 7 in which said means for inflating and deflating said oral balloon means includes a pilot tube extending along the proximal portion of said tube assembly and communicating with the interior of said oral balloon means.

13. The device of claim 7 in which said means for inflating said esophageal balloon means includes a pilot tube extending along said tube assembly and communicating with the interior of said esophageal balloon means.

14. The device of claim 1 in which said esophageal balloon means has along its outer surface at least one longitudinally-elongated electrode engageable with an area of the esophagus in direct alignment with a patient's heart; and means extending along said tube assembly for electrically charging said electrode for producing cardiac defibrillation.

15. The device of claim 14 in which said electrode comprises at least one conductive metal strip extending longitudinally along said balloon esophageal balloon means.

16. The device of claim 15 in which said electrode includes a plurality of electrically-interconnected metal strips extending along said balloon and arranged in circumferentially-spaced relation thereabout.

17. The device of claim 14 in which a pair of balloon-orienting electrodes are mounted upon said esophageal balloon means adjacent opposite ends thereof and in spaced relation with respect to said defibrillating electrode; and means extending along said tube assembly for operatively connecting each of said balloon-orienting electrodes with an electrocardiograph.

18. An esophago-pharyngeal airway device adapted for insertion through the mouth and into the esophagus of a patient to provide separate passages for stomach drainage and for artificial respiration, comprising an elongated flexible tube assembly including first tube means having a proximal end portion and a distal end portion for extending through said mouth and terminating in the stomach of a patient, and second tube means separate from said first tube means and having a proximal end portion adjacent the proximal end portion of said first tube means and a distal end portion for extending through the mouth and terminating proximal to the distal end portion of said first tube means and having an air flow port proximate the entrance of a trachea of a patient, said first tube means being a stomach drain tube, and said second tube means being an air tube, said first and second tube means being disposed in close parallel relation, said tube assembly further including a pair of pilot tubes disposed in parallel relation with said first and second tube means and each having distal and proximal end portions; an inflatable tubular oral balloon means extending about and sealed to said first and second tube means intermediate the end portions of said second tube means for engaging and urging the soft palate into sealing engagement with the posterior nasopharyngeal wall of a patient following insertion of said device and inflation of said oral balloon means; one of said pilot tubes communicating at its distal end with said oral balloon means to transmit air for inflating and deflating said balloon means and having its proximal end extending at least adjacent the proximal end portions of said first and second tube means; an inflatable and deflatable tubular esophageal balloon means spaced distally from said distal end of said air tube, and extending about and sealed to said drain tube for securingly engaging, upon inflation thereof, the wall of a patient's esophagus below the entrance to the trachea and above the stomach to prevent aspiration of refluxed contents of the stomach; said second tube means extending distally of said esophageal balloon means and terminating in at least one drainage inlet at its distal end, a second of said pilot tubes communicating at its distal end with said esophageal balloon to transmit air for inflating and deflating the same and having its proximal end extending at least adjacent the proximal end portions of said first and second tube means.

19. The device of claim 18 in which said air tube and said drain tube are disposed in side-by-side relation.

20. The device of claim 19 including permanent securing means for maintaining the side-by-side relation of said air tube and said drain tube.

21. The device of claim 19 in which said oral balloon is sealingly secured at its ends to said tube assembly.

22. The device of claim 18 in which said air tube has at least one port in communication with said oral balloon means.

23. The device of claim 18 in which said esophageal balloon means has along its outer surface at least one longitudinally-elongated electrode engageable with an area of the esophageal wall interposed between said esophageal balloon means and the patient's heart; and means for transmitting electrical current to said electrode for producing cardiac defibrillation.

24. The device of claim 23 in which said electrode comprises at least one conductive metal strip extending longitudinally along said esophageal balloon means.

25. The device of claim 24 in which said electrode includes a plurality of electrically-interconnected metal strips extending longitudinally along said esophageal balloon means and arranged in circumferentially-spaced relation thereabout.

26. The device of claim 23 in which a pair of additional electrodes are mounted upon said esophageal balloon means adjacent opposite ends of said balloon means and in spaced relation with respect to said first-mentioned electrode; and means extending along said tube assembly for operatively connecting each of said additional electrodes with an electrocardiograph.

27. An esophago-pharyngeal airway device adapted for insertion through the mouth and into the esophagus of an unconscious patient to provide at least one passage for artificial respiration, comprising a tube assembly including first tube means having a proximal end portion and a distal end portion for extending through the mouth and terminating in the stomach of a patient, and a second tube means separate from said first tube means and having a proximal end portion adjacent the proximal end portion of said first tube means and a distal end portion proximal to the distal end portion of said first tube means, said first tube means being an air tube and said second tube means being a guide tube; said first and second tube means being disposed in close parallel relation with said second tube means slidably receiving an elongated flexible tube means separate from said first and second tube means and having a distal end portion for extending through the mouth and terminating in the stomach of a patient and a proximal end portion adjacent the proximal end portions of said first and second tube means; an inflatable and deflatable tubular oral balloon means extending about and sealed to said first and second tube means intermediate the end portions of said first tube means for engaging and urging the soft palate into sealing engagement with the posterior nasopharyngeal wall of a patient following insertion of said device and inflation of said oral balloon means for inflating and deflating said oral balloon means; an inflatable and deflatable tubular esophageal balloon means extending about and sealed to said elongated flexible tube means intermediate the end portions thereof at a position spaced distally from said first tube means; and means for inflating and deflating said esophageal balloon means.

28. The device of claim 27 in which said elongated flexible tube is a stomach drain tube distal and proximal end portions.

29. The device of claim 28 in which said stomach drain tube extends distally of said esophageal balloon means and terminates in at least one drainage-receiving opening at its distal end.

30. The device of claim 28 in which said means for inflating said esophageal balloon includes a pilot tube extending along said tube assembly and communicating with the interior of said esophageal balloon means.

31. The device of claim 28 in which said esophageal balloon means is adapted for sealingly engaging, upon inflation thereof, the wall of a patient's esophagus below the entrance to the trachea to prevent aspiration of refluxed stomach contents and gastric inflation.

32. The device of claim 27 in which an oral flange member is externally mounted upon said tube assembly intermediate the ends of said air tube for sealingly engaging the face of a patient about the lips thereof.

33. The device of claim 32 in which said flange member is frictionally and slidably mounted upon said tube assembly.

34. The device of claim 27 in which said air tube and said guide tube are disposed in side-by-side relation.

35. The device of claim 34 including securing means for maintaining the side-by-side relation of said air tube and said guide tube.

36. The device of claim 35 in which said oral balloon means is sealingly secured at its ends to said tube assembly.

37. The device of claim 32 in which said air tube has at least one air flow port located distal to said oral balloon means.

38. The device of claim 37 in which said air flow port is disposed at the distal end of said air tube.

39. The device of claim 37 in which said means for inflating and deflating said oral balloon means includes a pilot tube extending along said tube assembly and communicating with the interior of said oral balloon means.

* * * * *

UNITED STATES PATENT AND TRADEMARK OFFICE
CERTIFICATE OF CORRECTION

PATENT NO. : 4,090,518

DATED : May 23, 1978

INVENTOR(S) : James O. Elam

It is certified that error appears in the above-identified patent and that said Letters Patent are hereby corrected as shown below:

Col. 1, line 57 change "is" to -- if --.

Col. 2, line 24 change "to" to -- so --.

Col. 4, line 48 change "ahd" to -- and --.

Col. 5, line 9 change "frinctionally" to -- frictionally --.

Col. 5, line 13 change "digital" to -- distal --.

Col. 5, line 36 change "esohageal" to -- esophageal --.

Col. 5, line 41 change "well" to -- wall --.

Col. 5, line 57 change "dii-" to -- di- --.

Col. 7, line 10 change "the" (first occurrence) to -- The --.

Col. 8, line 40 change "apporoximately" to -- approximately --.

Col. 8, line 65 change "advnaced" to -- advanced --.

Col. 11, line 22 change "meeans" to -- means --.

Col. 11, line 39, after "balloon" insert -- means --.

Col. 11, line 59 change "port air flow" to -- air flow port --.

Col. 11, line 64 change ":" to -- ; --.

Col. 12, line 29 delete "balloon" (first occurrence).

Col. 12, line 33 delete "balloon" and substitute -- esophageal balloon means --.

Col. 12, line 62 after "inflatable" insert -- and deflatable --.

Col. 13, line 8 change "securingly" to -- sealingly --.

UNITED STATES PATENT AND TRADEMARK OFFICE
CERTIFICATE OF CORRECTION

PATENT NO. : 4,090,518            Page 2 of 2

DATED : May 23, 1978

INVENTOR(S): James O. Elam

It is certified that error appears in the above-identified patent and that said Letters Patent are hereby corrected as shown below:

Col. 13, line 16 after "balloon" insert -- means --.

Col. 14, line 23 after "tube" insert -- having --.

*Signed and Sealed this*

*Twenty-fourth* Day of *October 1978*

[SEAL]

Attest:

RUTH C. MASON
*Attesting Officer*

DONALD W. BANNER
*Commissioner of Patents and Trademarks*